US00RE36043E

United States Patent [19]

Knighton

[11] E Patent Number: Re. 36,043

[45] Reissued Date of Patent: Jan. 12, 1999

[54] ENDOSCOPE AND METHOD FOR VEIN REMOVAL

[75] Inventor: David R. Knighton, Minneapolis, Minn.

[73] Assignee: Embro Vascular, L.L.C.

[21] Appl. No.: 585,410

[22] Filed: Jan. 11, 1996

Related U.S. Patent Documents

Reissue of:

[64] Patent No.: 5,373,840
Issued: Dec. 20, 1994
Appl. No.: 956,904
Filed: Oct. 2, 1992

[51] Int. Cl.[6] ..... A61B 1/00

[52] U.S. Cl. ..... 600/101; 600/104; 600/114; 606/157

[58] Field of Search ..... 600/101, 104, 600/106, 107, 183, 114; 606/157, 158, 159, 205, 207, 40, 49, 190, 198

[56] References Cited

U.S. PATENT DOCUMENTS

| | | |
|---|---|---|
| Re. 29,088 | 12/1976 | Shaw . |
| 1,867,624 | 7/1932 | Hoffman . |
| 2,001,169 | 5/1935 | Wallace . |
| 2,011,169 | 8/1935 | Wappler . |
| 2,028,635 | 1/1936 | Wappler . |

(List continued on next page.)

FOREIGN PATENT DOCUMENTS

| | | |
|---|---|---|
| 3942589 | 7/1991 | Germany . |
| 510235 | 5/1976 | U.S.S.R. . |
| 1123674A | 11/1984 | U.S.S.R. . |
| 1371689 A1 | 3/1986 | U.S.S.R. . |
| 2082459 | 3/1982 | United Kingdom . |
| 2195540 | 4/1988 | United Kingdom . |

OTHER PUBLICATIONS

DeLaria, G.A., et al., "Leg Wound Complications Associated With Coronary Revascularization", *J. Thorac. Cardiovasc. Surg.*, 81:403–407, 1981.

Dmitri et al., "A quick and atraumatic method of autologous vein harvesting using the subcutaneous extraluminal dissector", *J. Cardiovasc. Surg.* 28:103–111 (1987).

(List continued on next page.)

*Primary Examiner*—Beverly M. Flanagan
*Attorney, Agent, or Firm*—Popovich & Wiles, P.A.

[57] ABSTRACT

An endoscope for use in harvesting blood vessels includes a scope body of the type having a lumen extending longitudinally therethrough which itself has a proximal and a distal end. The endoscope includes means for viewing an area adjacent the distal end of the lumen, and the lumen has a lateral dimension of a size sufficient to accommodate the blood vessel being harvested and at least one tool for use in harvesting the blood vessel. A first end of the blood vessel section to be harvested is exposed through an incision in the patient's body. A dissecting tool and a gripping tool are inserted through the lumen of the endoscope and used to dissect the blood vessel away from the surrounding connective tissue of the patient's body, using the viewing means of the endoscope to view this dissection in process within the patient's body. Additional tools are provided for use through the lumen of the endoscope to remove body fluids and coagulate bleeding tissue, and to sever side branches from the blood vessel to be harvested, as well as to sever a distal end of the blood vessel to be harvested when a desired length of blood vessel has been dissected. Only a single small incision in the patient's body is necessary to harvest a relatively long length of blood vessel in a precise and controlled manner through endoscopic vision using the inventive endoscope and its related tools.

*The questions raised in reexamination request No. 90/004, 301, filed Jul. 12, 1996, have been considered and the results thereof are reflected in this reissue patent which constitutes the reexamination certificate required by 35 U.S.C. 307 as provided in 37 CFR 1.570(e).*

52 Claims, 8 Drawing Sheets

U.S. PATENT DOCUMENTS

| | | |
|---|---|---|
| 2,316,297 | 4/1943 | Southerland et al. . |
| 2,868,206 | 1/1959 | Stoesser . |
| 2,944,552 | 7/1960 | Cannon . |
| 3,185,155 | 5/1965 | Slaten et al. . |
| 3,336,916 | 8/1967 | Edlich . |
| 3,856,016 | 12/1974 | Davis . |
| 3,882,854 | 5/1975 | Hulka et al. . |
| 3,934,115 | 1/1976 | Peterson . |
| 4,038,987 | 8/1977 | Komiya . |
| 4,362,160 | 12/1982 | Hiltebrandt . |
| 4,369,768 | 1/1983 | Vukovic . |
| 4,440,170 | 4/1984 | Golden et al. . |
| 4,493,321 | 1/1985 | Leather . |
| 4,499,898 | 2/1985 | Knepshield . |
| 4,499,899 | 2/1985 | Lyons, III . |
| 4,516,575 | 5/1985 | Gerhard et al. . |
| 4,556,058 | 12/1985 | Green . |
| 4,586,919 | 5/1986 | Taheri . |
| 4,597,389 | 7/1986 | Ibrahim et al. . |
| 4,638,802 | 1/1987 | Okada . |
| 4,653,476 | 3/1987 | Bonnet . |
| 4,745,908 | 5/1988 | Wardle . |
| 4,759,348 | 7/1988 | Cawood . |
| 4,759,364 | 7/1988 | Boebel . |
| 4,762,120 | 8/1988 | Hussein . |
| 4,768,508 | 9/1988 | Chin et al. . |
| 4,793,346 | 12/1988 | Mindich . |
| 4,858,595 | 8/1989 | Buess et al. . |
| 4,862,874 | 9/1989 | Kellner . |
| 4,869,268 | 9/1989 | Yoon . |
| 4,877,016 | 10/1989 | Kantor et al. . |
| 4,932,952 | 6/1990 | Wojciechowicz, Jr. . |
| 4,997,436 | 3/1991 | Oberlander . |
| 5,013,312 | 5/1991 | Parins et al. . |
| 5,020,514 | 6/1991 | Heckele . |
| 5,037,433 | 8/1991 | Wilk et al. . |
| 5,047,038 | 9/1991 | Peters et al. . |
| 5,049,154 | 9/1991 | Quadri ..... 606/171 X |
| 5,213,093 | 5/1993 | Swindle . |
| 5,284,478 | 2/1994 | Nobles et al. . |
| 5,373,840 | 12/1994 | Knighton . |
| 5,425,355 | 6/1995 | Kulick . |
| 5,447,513 | 9/1995 | Davison et al. . |
| 5,549,637 | 8/1996 | Crainic |

OTHER PUBLICATIONS

Hauer et al., "Endoscopic subfacial discission of perforating veins", *Surgical Endosc.* 2:5–12 (1988).

Meldrum–Hanna et al., "Long Saphaneous Vein Harvesting", *J. Surg.* 56:923–924 (1986).

Moazami, Nader, Ph.D., et al., "Minimally Invasive Greater Saphenous Vein Harvesting for Coronary Artery Bypass Surgery", *Surgical Rounds,* pp. 94–98, Mar. 1997.

Rashid, A., et al., "Subcutaneous Technique for Saphenous Vein Harvest", *Ann. Thorac. Surg.,* 37(2):169–170, 1984.

Wheatley, D.J., ed., *Surgery of Coronary Artery Disease,* C.V. Mosby Co., pp. 348–349, 374–375.

"Incision Decision", Atrium Medical Corporation advertisement, appearing in *J. Thorac. Cardiovasc. Surg.,* 83(4), 1982.

"Saphenous vein grafts are number 1. Period.", Atrium Medical Corporation advertisement, appearing in *J. Thorac. Cardiovasc. Surg.,* 81(6), 1982.

"The in Situ Saphenous Vein Arterial; Bypass by Valve Incision," R. P. Leather et al., *Vascular Surgical Techniques An Atlas,* 1989, pp. 255–262.

"Reversed Saphenous Vein for Femoropopliteal Bypass Grafting," K. G. Burnand, *Vascular Surgical Techniques An Atlas,* K. G. Burnand et al., 1989, pp. 228–234.

"Angioscopic Preparation for Saphenous Vein in Situ Bypass Grafting," A. K. Chin et al.,*Endovascular Surgery,* 1989, pp. 74–81.

J. Sklar Mfg. Co., Inc., "Surgical Instruments", Long Island City, NY; 1973.

Loré, John Marion, "Tender Grip Forceps", American Journal of Surgery; vol. 104; 7/1962. h .

ENDOSCOPE AND METHOD FOR VEIN REMOVAL

Matter enclosed in heavy brackets [ ] appears in the original patent but forms no part of this reissue specification; matter printed in italics indicates the additions made by reissue.

BACKGROUND OF THE INVENTION

The present invention relates generally to surgical instruments. In particular, the present invention relates to a method and instrument for harvesting a section of a blood vessel from a patient.

In certain surgical procedures, it is necessary to remove a section of a blood vessel from a patient for use in another part of the patient's body or for transplanting into a second patient's body. For example, a section of the saphenous vein may be removed for use in coronary bypass surgery. Previously, it has been necessary to make an incision along the full length of the vein section to be removed. The vein is then freed by severing and ligating the branches of the vein, after which the section of the vein can be removed from the patient. The full length incision must then be closed, for example by suturing or staples. Obviously, the harvesting of the vein in this manner leaves disfiguring scars which are cosmetically undesirable. Additionally, the large incision creates a risk of infection to the patient and may not heal properly, especially with those patients who have poor circulation in their extremities. Such an incision may create a chronic wound which will not heal.

Devices for harvesting a section of a blood vessel without creating a full length incision have been suggested. U.S. Pat. No. 4,793,346 to Mindich discloses a device for harvesting a section of a blood vessel by making only small incisions at opposite ends of the blood vessel section. The device includes a guide rod which fits inside of the vein section and a tube having an inner diameter slightly larger than the outer diameter of the vein section to be harvested. The tube has one or more knife blades at the leading edge which are connected to an electrical supply. The vein section is removed by making the incision sufficiently deep so as to expose the ends of the blood vessel section to be harvested. The blood vessel is cut to expose one end, the guide rod is inserted inside the blood vessel section, and the tube is placed over the end of the blood vessel section to be removed. The tube is then pushed along the blood vessel (into the patient) while rotating the tube to sever the branches of the blood vessel with the knife blades mounted at the leading edge of the tube. Electrical current is supplied to the knife blades to heat the blades and thereby cauterize the ends of the severed branches of the blood vessel. The procedure is continued until the tube has reached the second of the two incisions. The blood vessel is exposed and cut from the patient at the second incision, and the tube is then removed from the patient with the blood vessel section inside of the tube. The blood vessel section is then removed from the tube for further treatment and used as desired.

UK Patent Application GB 20 82 459A discloses a device for harvesting a section of a blood vessel similar to that disclosed in the Mindich patent. Again, two incisions are made, one at each end of the blood vessel section to be harvested. A guide rod is inserted into the blood vessel section through one of the incisions and a tube having a cutting element at its operative end is passed over the blood vessel section and guide rod assembly. The tube is rotated as it passes over the blood vessel section to sever the connecting branches. After the tube has passed the entire length of the blood vessel section, the section is cut away through the second incision and the tube is removed from the patient with the harvested section inside the tube.

The blood vessel harvesting devices of the prior art have certain distinct disadvantages. While the prior art devices eliminate the need for a full length incision to remove the blood vessel segment, two incisions, one at each end of the segment to be harvested, are required in order to remove the blood vessel segment. For patients likely to develop chronic wounds, each additional incision increases the risk to the patient, and it is desirable to keep such incisions as close to the patient's trunk as possible and to minimize the number and size of such incisions. Additionally, the prior art devices do not allow for the viewing of the dissection of the blood vessel segment. The physician operating the removal device is unable to see the progression of the dissection and must rely on the guide rod inserted within the blood vessel to guide the cutting instrument in the proper direction. The inability to view the dissection directly increases the risk of damaging the blood vessel segment and the risk of causing injury to the patient.

In addition, it is critical that the segment of blood vessel being harvested is handled with great care since it is destined for reuse (e.g., as an arterial bypass). The blind insertion of a guide rod into the blood vessel damages and likely destroys the endothelium of the vessel. The prior art devices also have the disadvantage of being unable to adequately close off severed branches of the blood vessel and thus are unable to adequately control bleeding. As a result, the patient suffers greater blood loss than is necessary. The prior art devices also may remove more tissue than is necessary because the size of the cutting device is not readily adaptable to changes in the size of the blood vessel.

There is a need for an efficient and effective means for harvesting a section of a blood vessel from the body of a patient. Specifically, there is a need for a device that does not require insertion of any component within the vessel being harvested, and that allows direct viewing of the dissection of the blood vessel segment while at the same time minimizing the size of the incision into the patient's body. Such a device would allow the physician to be much more precise in this procedure, minimize the risk of the patient developing a chronic wound that will not heal, minimize the amount of scarring to the patient's body and maintain the internal integrity of the blood vessel being harvested.

SUMMARY OF THE INVENTION

The present invention is a device and method for harvesting a section of a blood vessel from a patient's body. The invention includes an endoscope of the type having a scope body with a lumen extending longitudinally therethrough, with the lumen having a proximal end and a distal end. The endoscope includes means for viewing an area adjacent to the distal end of the lumen. The lumen has a lateral dimension of size sufficient to accommodate a blood vessel and at least one tool for use in harvesting the blood vessel.

This endoscope for harvesting a blood vessel is relatively uncomplicated. The endoscope allows a section of a blood vessel to be removed by making only a small incision at one end of the blood vessel section to be harvested. The incision exposes a first end of the blood vessel section to be harvested and the first end is inserted through the lumen of the endoscope. The blood vessel is then dissected away from surrounding connective tissue of the patient's body with a dissecting tool inserted through the lumen of the endoscope, using the viewing means to view the dissection in process as the endoscope is advanced along the blood vessel into the patient's body.

In one preferred embodiment, the endoscope is used with a tool for ligating and cutting branches of the blood vessel segment or a second end of the blood vessel segment. The tool has a distal operative tip with means on the distal tip for applying a ligation clip to a section of the blood vessel specimen which is to be sealed. There are also means on the distal tip for cutting the blood vessel segment between the clip and the first end of the blood vessel segment. The tool eliminates the requirement of making a second incision at the second end of the blood vessel segment to cut the blood vessel segment at the second end so that it may be removed.

The endoscope is ideally suited for patients likely to develop chronic wounds, such as diabetics or other persons with poor circulation, because only one small incision is required to remove the blood vessel segment. The endoscope also allows the physician to directly view the dissection of the blood vessel segment. The ability to directly view the dissection allows the physician to conduct the vessel harvesting procedure much more efficiently and precisely, minimizing the risk of damage the blood vessel and minimizing the risk of injury to the patient.

BRIEF DESCRIPTION OF THE DRAWINGS

The invention will further be described with reference to the accompanying drawings where like numbers refer to like parts in several views, and wherein.

While the above-identified drawing figures set forth one preferred embodiment of the invention, other embodiments are also contemplated, as noted in the discussion. In all cases, this disclosure presents the present invention by way of representation and not limitation. It should be understood that numerous other modifications and embodiments can be devised by those skilled in the art which fall within the scope and spirit of the principles of this invention. It should be specifically noted that the figures have not been drawn to scale as it has been necessary to enlarge certain portions for clarity.

DETAILED DESCRIPTION OF THE PREFERRED EMBODIMENTS

The present invention is a device and method for harvesting a section of a vessel from a patient's body for use in another part of the patient's body or for transplanting into a second patient's body. For example, a section of the saphenous vein may be removed for use in coronary bypass surgery. The blood vessel needs to be removed without undue damage to the blood vessel, as well as with minimal damage and trauma to the patient. Although the description herein is directed to the harvesting of the saphenous vein, it is contemplated that the present invention be used in connection with the efficient and effective harvesting of the other lumens and vessels from a patient's body.

THE TOOLS

Figure 1:
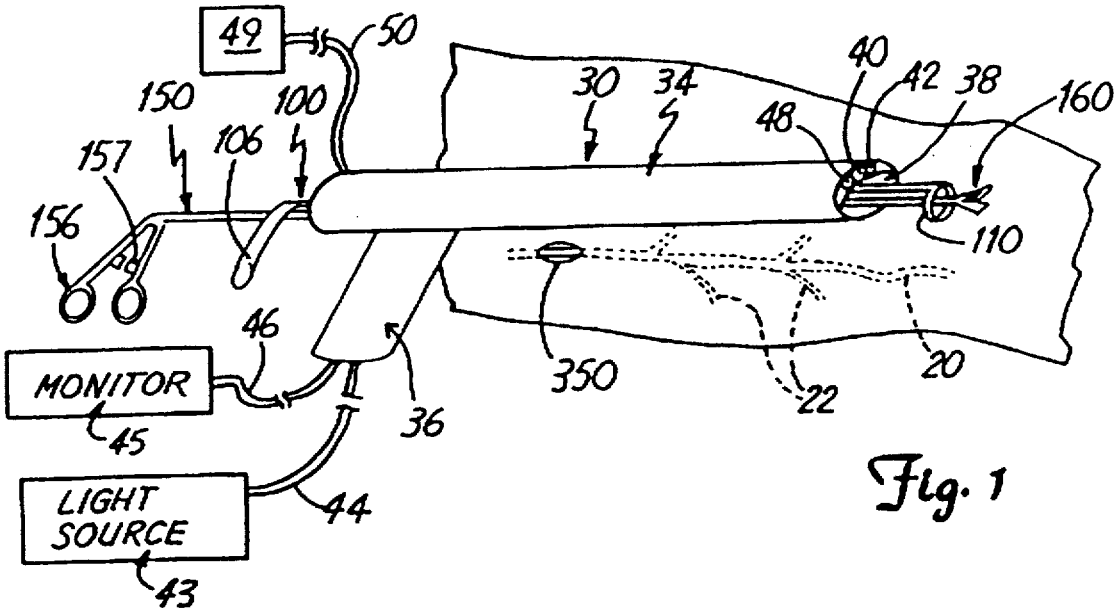
FIG. 1 is a perspective view of the inventive endoscope and some related tools, along with a portion of a patient's leg.

In FIG. 1, a saphenous vein 20 (shown in phantom) and endoscope 30 are shown. The saphenous vein 20 travels along the medial side of the foot, leg, and thigh, where it joins with the femoral vein near the groin.

Figure 2:
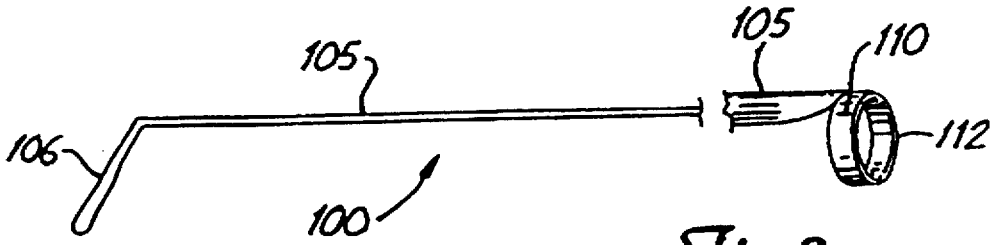
FIG. 2 is a side elevational view of a dissecting tool of the present invention, with its distal end enlarged in perspective.
Figure 3:
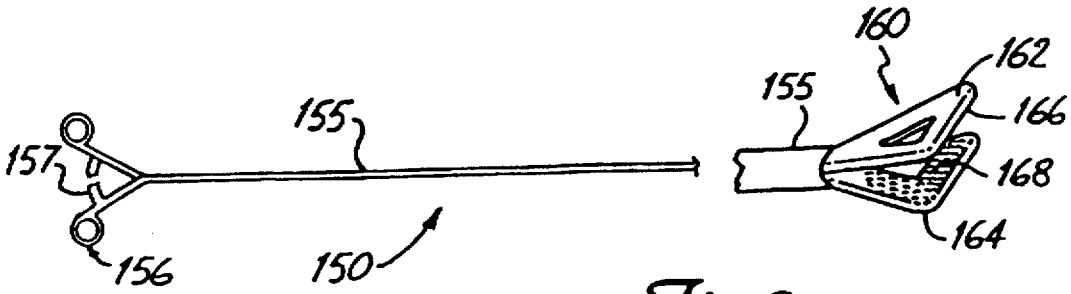
FIG. 3 is a side elevational view of a gripping tool of the present invention, with its distal end enlarged in perspective.

When used to harvest a blood vessel, the endoscope 30 is used in conjunction with several tools. A dissecting tool 100 (FIG. 2) is used to separate the blood vessel from the surrounding connective tissue. A gripping forceps 150 (FIG. 3) is used by the physician to hold the blood vessel 20 during the procedure. A ligation-cutting tool 200 (FIG. 4) is used when severing side branches 22 from the blood vessel 20. A side-biting ligation-cutting tool 250 (FIG. 5) is used to transect the blood vessel 20 when the dissection is completed. Finally, a suction-coagulator tool 300 (FIG. 6) is used to control bleeding during the procedure. Each of these tools is described in detail in the succeeding discussions.

Figure 7:
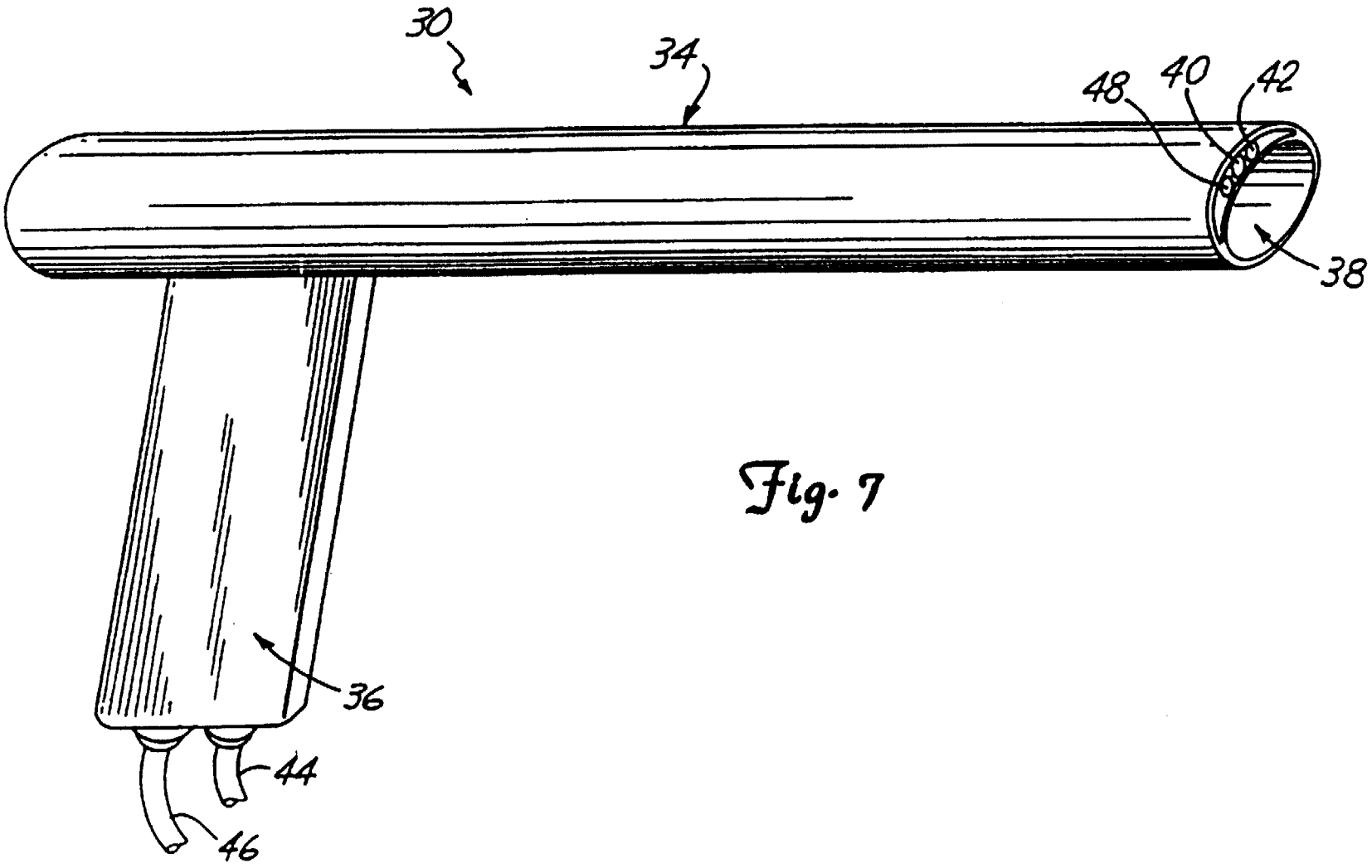
FIG. 7 is an enlarged perspective view of the endoscope of the present invention.
Figure 8:
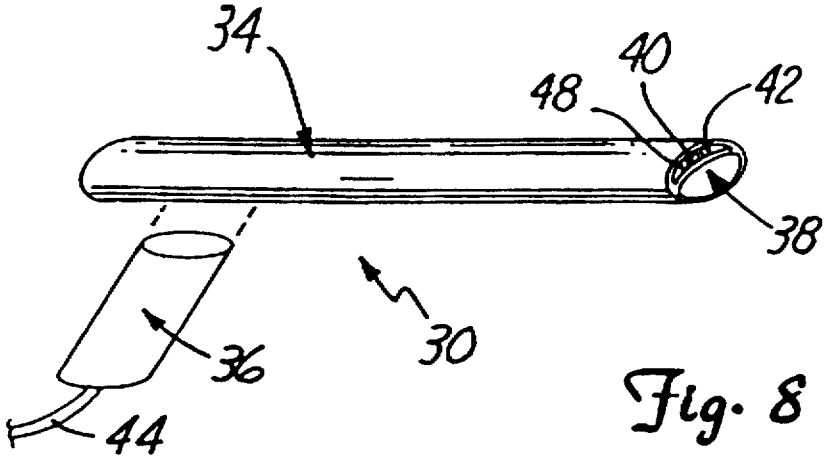
FIG. 8 is a perspective view of the endoscope of the present invention, showing its two-part assembly.

As illustrated in FIGS. 1 and 7, the endoscope 30 includes an elongated scope body 34 and a handle 36. A lumen 38 extends longitudinally through the scope body 34 and has a cross-sectional shape which is substantially elliptical. The lumen 38 is of a size large enough to accommodate the blood vessel 20 which is to be harvested and one or more of the tools 100, 150, 200, 250 and 300 longitudinally therein. In one embodiment, the size of the lumen 38 in the scope body 34 is 2 cm wide by 1 cm deep in an elliptical shape, while the scope body 34 itself is 30 to 90 centimeters long. Each of the tools is at least 2 cm longer than the scope body 34. As illustrated in FIG. 8, the scope body 34 of the endoscope 30 is selectively securable to the handle 36. The scope body 34 can thus be made as a disposable unit to eliminate problems with re-sterilization of the portion of the endoscope 30 that enters the patient's body. After use, the endoscope is disassembled, the scope body 34 disposed of, and the handle 36 (containing power connections, lighting means, etc.) saved for repeated use with a new scope body. Alternatively, the scope body has a longitudinal channel therein for reception of the viewing and illumination portions of the endoscope, so that those components are reused while the scope body is disposed after each use. The scope body is provided in a variety of lengths and sizes (cross-sectional) to accommodate patients of different sizes and different blood vessel lengths.

As seen in FIG. 7, fiber optics illumination source 40 and a fiber optics viewing device 42 are located at the distal end of the endoscope 30 and positioned adjacent each other such that the area immediately adjacent the distal end of endoscope 30 can be illuminated and viewed by the physician. When connected to the handle 36, the source 40 is operably connected to an external light source 43 by a suitable light transmission conduit 44 which extends through the endoscope 30. Similarly, the viewing device 42 is operably connected to an external monitor 45 by a suitable image transmission conduit 46 which extends through the endoscope 30. The physician views the area adjacent the distal end of endoscope 30 using the illumination source 40 and the viewing device 42 by use of the viewing monitor 45 (FIG. 1) which is connected to the endoscope handle 36 through the conduit 46. The monitor 45 may take several forms, such as a television monitor or an eye-piece worn by the physician, as is conventional. The endoscope body 34 also has an irrigation channel 48 extending therethrough. The irrigation channel is operably coupled to an external source of irrigant 49 via a suitable conduit 50. A distal open end of the irrigation channel is positioned adjacent the distal ends of the fiber-optic illumination source 40 and the viewing device 42, as seen in FIG. 1.

Each of the tools 100, 150, 200, 250 and 300 to be used with the endoscope 30 are of a size small enough to fit through the lumen 38 of the scope body 34 while a blood vessel 20 is also in the lumen 38. The tools 100, 150, 200, 250 and 300 are also long enough to allow the physician to comfortably manipulate them through the lumen 38 (i.e., the tools 100, 150, 200, 250 and 300 are longer than the lumen 38).

The dissecting tool 100 (FIG. 2) is used to aid in separating the vessel being harvested from the surrounding tissue. The dissection tool 100 has an elongated shaft 105, with a handle 106 attached to the proximal end of the shaft 105 and an annular dissecting ring 110 attached to the distal end of shaft 105. The dissecting ring 110 is oriented such that a plane defined by the dissecting ring 110 is generally perpendicular to the longitudinal axis of the shaft 105. The size of dissecting ring 110 is large enough to fit over the exterior of the blood vessel 20. The dissecting ring 110 has a rounded distal edge 112 used to separate the blood vessel 20 from the surrounding connective tissue as the dissecting tool 100 is advanced over the blood vessel 20. The dissecting tool 100 is provided in a plurality of sizes for different sizes of blood vessels. Typical sizes for such tools would have inside diameters of 4 mm, 5 mm, and 6 mm.

The gripping tool 150 (FIG. 3) is used to hold and retain the vessel being harvested during the procedure. The gripping tool 150 has an elongated shaft 155, with a handle 156 attached to a proximal end of the shaft 155 and a gripping mechanism 160 attached to a distal end of the shaft 155. The handle 156 is preferably a scissors-type handle to actuate the gripping mechanism 160 at the distal end of the body 158 and includes a latching mechanism 157 which allows the gripping mechanism to be locked in a set position (e.g., in a "gripping" position). The shaft 155 transmits the actuating movement from the handle 156 to the gripping mechanism 160. The gripping mechanism 160 includes a first jaw 162 and a second jaw 164 which oppose each other. When the gripping handle 156 is operated by the physician, the first jaw 162 and the second jaw 164 are moved toward each other and may be used to grip the blood vessel 20 between gripping surfaces 166 and 168 thereon. The jaws 162 and 164 are small enough to fit through the dissecting ring 110 on the dissecting tool 100.

The ligation-cutting tool 200 (FIGS. 4, 4A and 4B) is used to sever and seal side branches on the vessel being harvested. The ligation-cutting tool 200 has an elongated shaft 201, with a ligation clip applicator 202 and a cutting mechanism 204 at the distal end of the shaft 201. The ligation clip applicator 202 includes a first yoke 208 and a second opposed yoke 210. Each yoke 208 and 210 is in turn divided into two sections; each yoke 208 and 210 is forked at its distal end, forming two opposed prongs 212A and 212B on the yokes 208 and 210, respectively. The prongs 212A and 212B on yokes 208 and 210 are parallel to each other and generally aligned with the longitudinal axis of the ligation-cutting tool 200. The yoke 208 and 210 and the prongs 212A and 212B thereon oppose each other and serve to apply ligation clips 216 (see FIGS. 4A and 4B) to a side branch 22 being severed. The opposing prongs 212A and 212B of each yoke 208 and 210 contain grooves 214A and 214B, respectively, to securely hold a ligation clip 216 therein. When the ligation clips 216 are thus held between the opposing prongs 212A and 212B of yokes 208 and 210, the generally U-shaped ligation clips 216 aid the physician in properly aligning the ligation-cutting tool 200 and the side branch 22 to be ligated by providing an abutment for the side branch 22 when the side branch 22 is positioned between the yokes 208 and 210. When the yokes 208 and 210 are biased towards each other in a conventional manner, the ligation clips 216 are deformed to clamp onto the side branch 22 therebetween and the blood flow through the side branch 22 is halted at two slightly spaced apart points (e.g., two clips are applied approximately 0.25 inches apart). When the ligation clip applicator 202 is activated and the yokes 208 and 210 clamp the ligation clips 216 onto the side branch 22, the side branch 22 is also held securely for cutting the side branch 22.

Figure 4:
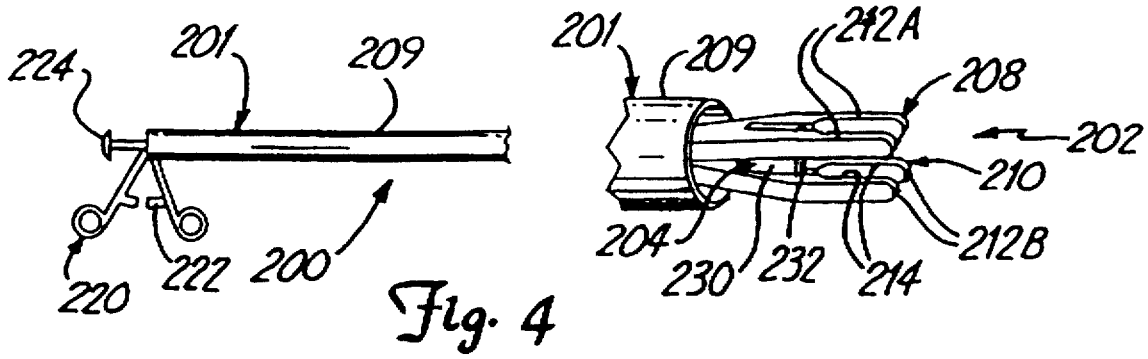
FIG. 4 is a side elevational view of a ligation-cutting tool of the present invention, with its distal end shown enlarged in perspective.
Figure 4A:
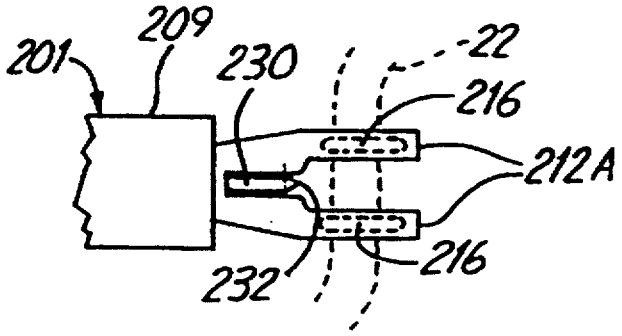
FIG. 4A is a top plan view of the distal end of the ligation-cutting tool of FIG. 4.
Figure 4B:
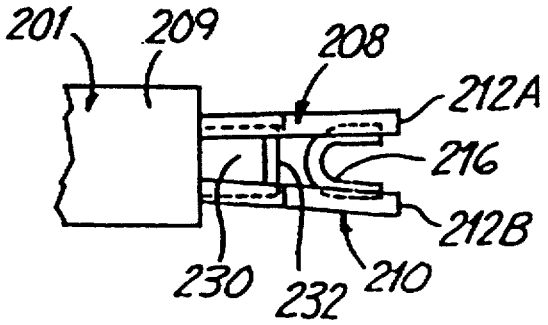
FIG. 4B is a side elevational view of the distal end of the ligation-cutting tool of FIG. 4.

The cutting mechanism 204 on the ligation-cutting tool 200 includes a cutting blade 230 aligned between the prongs 212A and 212B and proximal to the ligation clips 216. The cutting blade 230 is normally retracted (as seen in FIGS. 4, 4A and 4B) to allow the side branch 22 to be positioned properly between the yokes 208 and 210. A cutting edge 232 of the blade 230 faces the distal end of the ligation-cutting tool 200, and the cutting motion of the blade 230 is in a distal direction (e.g., towards the side branch 22). The blade 230 is wide enough to completely sever the side branch 22 between the two yokes 208 and 210. The cutting mechanism 204 is activated by the physician (as described below) after the side branch 22 has been ligated (i.e., the side branch 22 has been clipped shut and blood flow halted) and while the side branch is still held securely in the yokes 208 and 210. After the blade 230 has severed the side branch 22, the blade 230 returns into its original retracted position.

The ligation clip applicator 202 and the cutting mechanism 204 are both actuated by mechanisms at the proximal end of the shaft 201 of the ligation-cutting tool 200. The ligation clip applicator 202 is preferably actuated by a scissors-type handle 220. By squeezing the scissors-type handle 220, the physician causes each set of prongs 212A and 212B on the yokes 208 and 210 to be moved together, thereby compressing their respective ligation clips 216 about the side branch 22 of the blood vessel 20, as described above. The scissors-type handle 220 includes a latching mechanism 222 which serves to secure the handle 220 and thus the ligation clip applicator 202 in a closed or clamped position. While the ligation clip applicator 202 is held in a clamped position, the cutting mechanism 204 is actuated, preferably by a plunger 224 located at the proximal end of the ligation-cutting tool 200. The plunger 224 is operably connected to the cutting blade 230, and biased proximally to urge the blade 230 into its normally retracted position. By moving the plunger 224 distally, the physician causes the cutting blade 230 to likewise move distally and cut the side branch 22 of the blood vessel 20 which is retained between the yokes 208 and 210. When the physician releases the plunger 224, the plunger 224 (and thus the cutting blade 230) retracts to its original position. Manipulation of the handle 220 then separates the prongs 212A and 212B, leaving the clip in place on the severed portions of the side branch 22, and the ligation-cutting tool 200 is removed or relocated for reuse (the clips may be fed into place in the grooves of the prongs from a suitable clip magazine (not shown) to enable multiple ligations without removing the tool from the body).

The shaft 201 of the ligation-cutting tool 200 is a slender member that is longer than the lumen 38 of the endoscope 30. A housing 209 covers those mechanisms on the shaft 201 that transmit the manipulations of the handle 220 and the plunger 224 at the proximal end of the ligation-cutting tool 200 to the clipping and cutting motions, respectively, at the distal end of the ligation-cutting tool 200.

Figure 5:
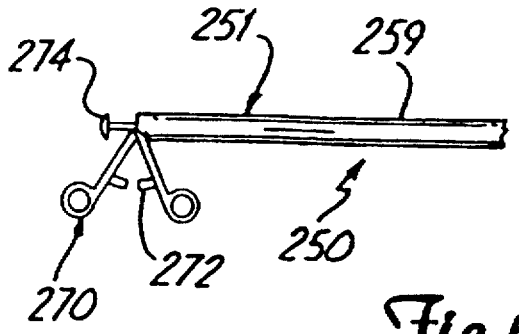
FIG. 5 is a side elevational view of a side-biting ligation-cutting tool of the present invention, with its distal end enlarged in perspective.
Figure 6:
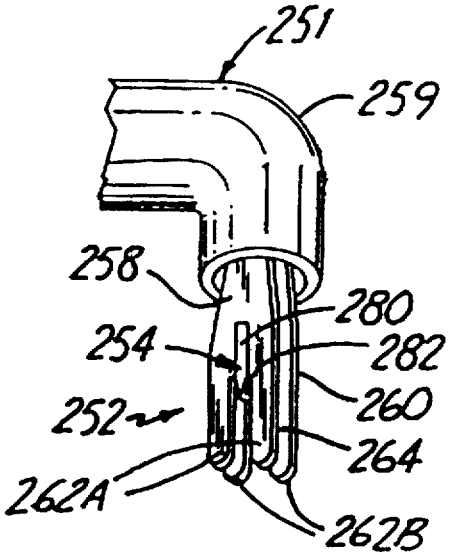
FIG. 6 is a side elevational view of a suction-coagulator tool of the present invention.
Figure 6:
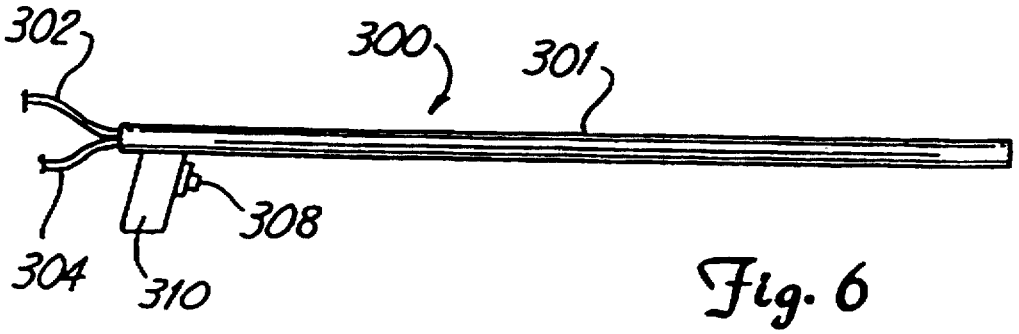

The side biting ligation-cutting tool 250 (FIG. 5) is used to sever and seal the distal end of the vessel being harvested. The side-biting ligation-cutting tool 250 is identical in operation to the ligation tool 200, except that the operative components at the distal end of the tool 250 are oriented generally normally to the axis of the tool 250. As seen in FIG. 5, the side biting ligation-cutting tool 250 has an elongated shaft 251, with a ligation clip applicator 252 and a cutting mechanism 254 at the distal end of shaft 251. The ligation clip applicator 252 includes a first yoke 258 and a second, opposed yoke 260. Each yoke in turn is forked at its distal end, forming two opposed prongs 262A and 262B, respectively. The prongs are aligned generally parallel and each has inner grooves 264 to retain ligation clips between each opposed pair of prongs 262A and 262B. The structure and operation of the ligation clip applicator 252 is similar to that illustrated in FIGS. 4A and 4B for the ligation-cutting tool 200.

The yokes 258 and 260 and the prongs 262A and 262B thereon oppose each other and serve to apply ligation clips (not shown in FIG. 5) to the distal end of the segment of the blood vessel being severed. When the ligation clips are thus held between the opposing prongs 262A and 262B of yokes 258 and 260, the generally U-shaped ligation clips aid in positioning and properly aligning the side biting ligation-cutting tool 250 and the blood vessel to be transected by providing an abutment for the blood vessel when the blood vessel is positioned between the yokes 258 and 260. When the yokes 258 and 260 are moved towards each other, the ligation clips are clamped onto the blood vessel therebetween and the blood flow through the blood vessel is halted at two slightly spaced-apart points (e.g., two clips are applied approximately 0.25 inches apart). When the ligation clip applicator 252 is activated and the yokes 258 and 260 clamp the ligation clips onto the blood vessel, the blood vessel is also held securely for cutting the blood vessel.

The cutting mechanism 254 on the side biting ligation cutting tool 250 includes a cutting blade 280 aligned between the prongs 262A and 262B. Again, the structure of the cutting mechanism for the tool 250 is quite similar to that illustrated in FIGS. 4A and 4B for the ligation-cutting tool 200. The blade 280 is positioned such that a cutting edge 282 of the blade 280 does not interfere with the alignment of the blood vessel between the yokes 258 and 260. The cutting blade 280 is normally retracted (as seen in FIG. 5) to allow the blood vessel to be positioned properly between the yokes 258 and 260. The cutting edge 282 of the blade 280 faces in a transverse direction from the shaft 251 of the side biting ligation-cutting tool 250, and the cutting motion of the blade 280 is in a transverse direction (e.g., toward the blood vessel). The blade 280 is wide enough to complete sever the blood vessel between the two yokes 258 and 260. The cutting mechanism 254 is activated after the blood vessel has been ligated (i.e., the blood vessel has been clipped shut and blood flow halted) and while the blood vessel is still held securely in the yokes 258 and 260. After the blade 280 has severed the blood vessel, the blade 280 returns to its original retracted position.

The primary difference between the tool 200 and tool 250 is that the distal operative portion of the tool 250 is oriented at an angle generally ninety degrees opposed to the axis of the shaft 251 of the tool 250. The yokes 258 and 260 are thus oriented to straddle a blood vessel extending generally parallel to the shaft 251 to apply ligation clips thereto. After clips are applied, the yokes continue to hold the blood vessel to permit severing of the vessel using the blade 280. Other than the revision in orientation of the distal portion of the ligation-cutting tool 250, it operates in the same manner as the ligation-cutting tool 200.

The ligation clip applicator 252 and the cutting mechanism 254 are both actuated by mechanisms at the proximal end of the shaft 251 of the ligation-cutting tool 250. The ligation clip applicator 252 is preferably actuated by a scissors-type handle 270. Squeezing of the scissors-type handle 270 causes each pair of prongs 262A and 262B on the yokes 258 and 260 to move together, thereby compressing their respective ligation clips about the blood vessel. The scissors-type handle 270 includes a latching mechanism 272 which serves to secure the handle 270 and thus the ligation clip applicator 252 in a closed or clamped position. While the ligation clip applicator is held in a clamped position, the cutting mechanism 254 is actuated, preferably by a plunger 274 located at the proximal end of the ligation-cutting tool 250. The plunger 274 is operably connected to the cutting blade 280, and biased proximally to urge the blade 280 into its normally retracted position. By moving the plunger 274 distally, the physician causes the cutting blade 280 to likewise move distally and cut the blood vessel which is retained between the yokes 258 and 260. When the physician releases the plunger 274, the plunger 274 (and thus the cutting blade 280) retracts to its original position. Manipulation of the handle 270 then separates the prongs 262A and 262B, leaving the clips in place on the severed portions of the blood vessel, and the ligation cutting tool 250 is removed.

The shaft 251 of the side biting ligation-cutting tool 250 is a slender member that is longer than the lumen 38 of the endoscope 30. A housing 259 covers those mechanisms on the shaft 251 that transmit the manipulations of the handle 270 and the plunger 274 at the proximal end of the side biting ligation-cutting tool 250 to the clipping and cutting motions, respectively, at the distal end of the side biting ligation-cutting tool 250.

The suction-coagulator tool 300 (FIG. 6) is used to remove body fluids (e.g., blood) and reduce bleeding during the vessel harvesting procedure, and is of the type generally known in the art for this procedure. The suction-coagulator tool 300 has an elongated shaft 301 and includes a handle 310 attached to the proximal end of shaft 301. A suction tube 302 is attached to the proximal end of shaft 301 and extends to the distal end of shaft 301. At the distal end of shaft 301 the suction tube 302 is open for suctioning body fluids. Also attached to the proximal end of shaft 301 is a power cable 304 for supplying power for tissue coagulation. When button 308 on handle 310 is activated, the power is supplied to the distal end of shaft 301 to cauterize bleeding tissue, and thus to stop bleeding. The suction-coagulator tool 300 controls bleeding in two ways. The suction tube 302 may be used alone to suction any body fluids from the dissection area, or the coagulator may be used to cauterize the bleeding tissue.

METHOD OF USE

Figure 9:
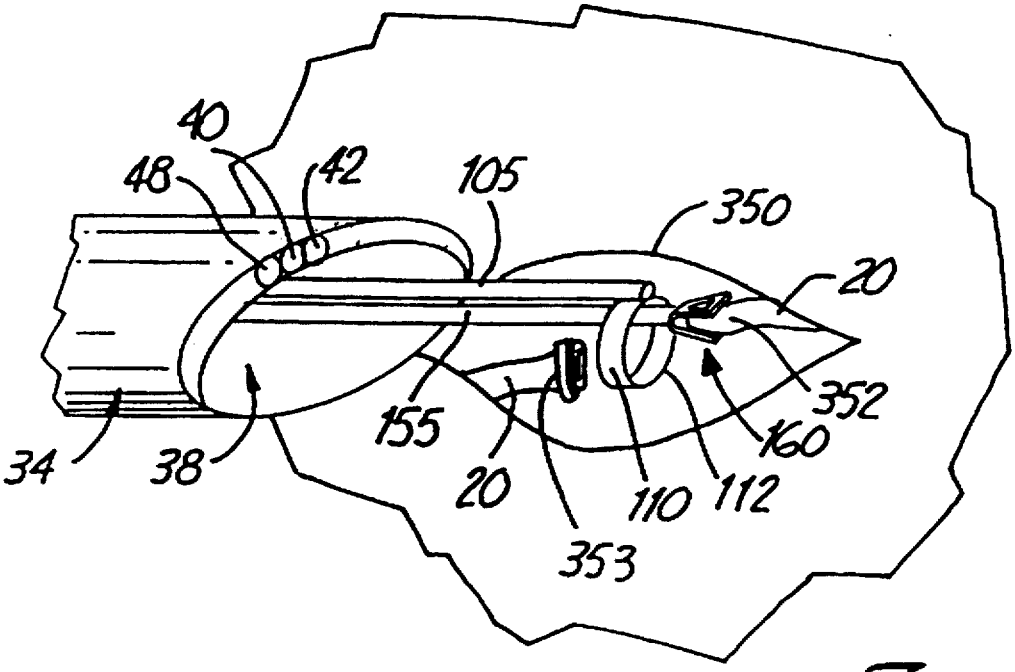
FIGS. 9–13 are enlarged perspective illustrations showing the distal end of the inventive endoscope and the tools of FIGS. 2–6 in use during the harvesting of a blood vessel.

The endoscope 30 and accompanying tools 100, 150, 200, 250 and 300 are used in combination for harvesting a vessel. After proper preparation of the incision site, the physician makes a small incision 350 (e.g., 3 cm long) over the proximal aspect of the blood vessel to be harvested (see FIGS. 1 and 9). The blood vessel 20 is exposed and dissected for a short length under direct vision. As seen in FIG. 9, the blood vessel 20 is then severed to expose a free end 352 and a free end 353 (which may be clipped as shown in FIG. 9). For example, to remove a saphenous vein, the incision 350 will be made at the groin over the saphenous vein and the vein will be dissected free from the junction of the common femoral vein. As shown in FIGS. 1 and 9, the gripping forceps 150 is inserted through the dissecting ring 110 of the dissecting tool 100, and the assembly of the dissecting tool 100 and the gripping forceps 150 is inserted through the lumen 38 of the endoscope 30 such that the distal ends of the dissecting tool 100 and gripping forceps 150 extend beyond the distal end of the lumen 38. The physician then grasps the free end 352 of the blood vessel 20 with the gripping forceps 150 and holds it under tension. The dissecting tool 100 is then advanced distally (together with the endoscope 30) over the distal end of the gripping forceps 150 and over the blood vessel 20. As the dissecting tool 100 is manipulated by the physician, the blood vessel 20 is dissected away from the surrounding connective tissue.

Figure 10:
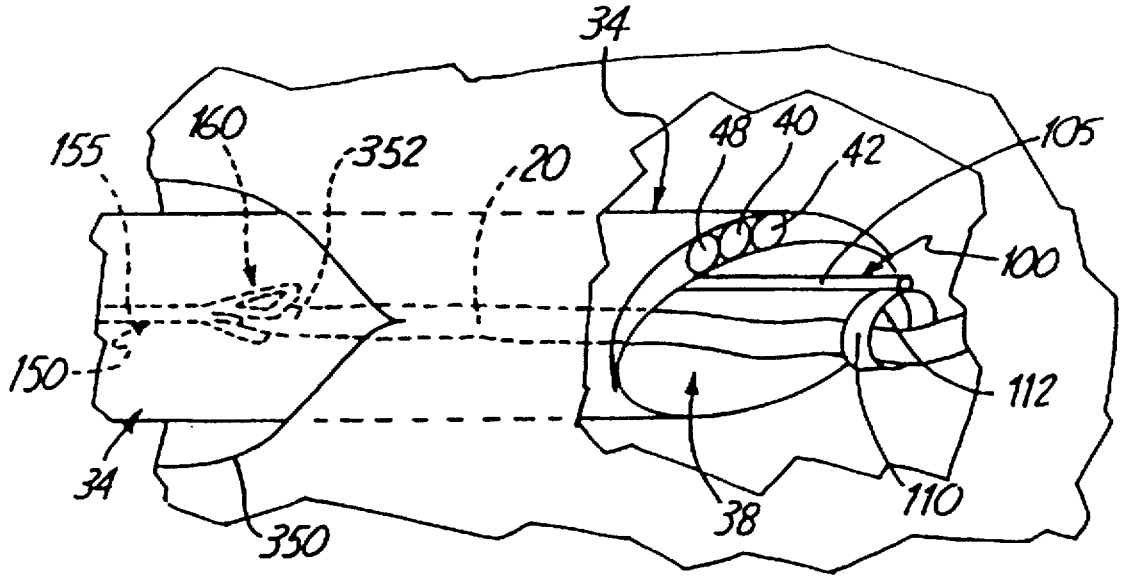

As illustrated in FIG. 10 (which has a portion of the patient's body broken away to show the invention in operation), the dissection process proceeds distally along the blood vessel 20, and the endoscope 30 is advanced along with the dissecting tool 100 into the incision 350. Until this point, the physician has been viewing the procedure under direct vision. Now, the physician switches to viewing the dissection process (occurring at the area immediately adjacent the distal end of the lumen 38) through the fiber optic viewing device 42 located at the distal end of the scope body 34 of the endoscope 30. The illumination source 40 provides adequate lighting for the physician to view the dissection and tool operations occurring within the patient via the monitor. Irrigant is introduced as necessary through the irrigation channel 48 of the endoscope 30 to keep blood or other body tissue from obscuring vision adjacent the distal end of the scope body 34 of the endoscope.

As the dissection tool 100 is advanced along the blood vessel 20, a side branch 22 of the blood vessel 20 may be encountered before the desired length of blood vessel 20 has been dissected. When the physician reaches a side branch 22 before obtaining the desired length of blood vessel 20, the ligation-cutting tool 200 is employed to sever the side branch 22 from the vessel being harvested (blood vessel 20).

Figure 11:
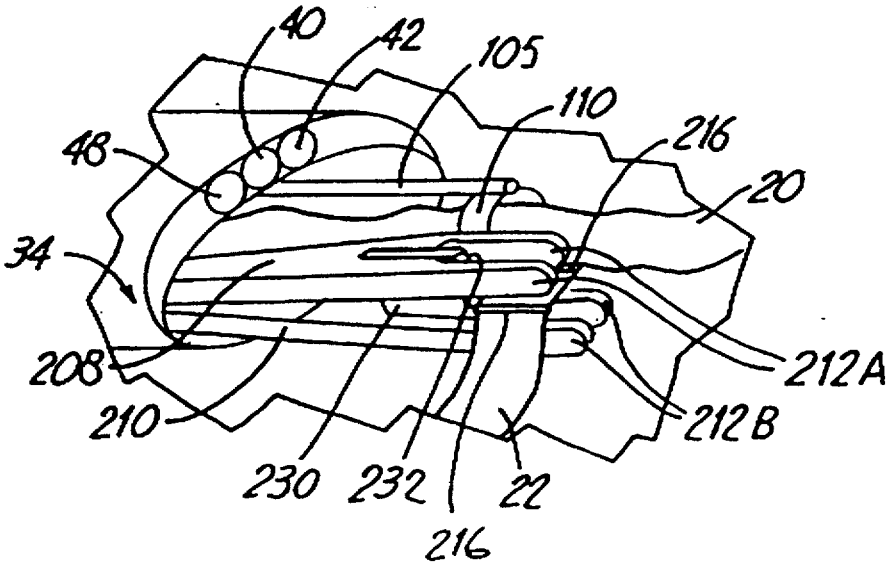

When a side branch 22 is reached, the physician stops advancing the dissecting tool 100 and endoscope 30 and, if necessary, withdraws the dissecting tool 100 proximally from the side branch 22 to provide room for operation of the ligation-cutting tool 200. The ligation-cutting tool 200 is inserted into the proximal end of the lumen 38 and advanced distally through the lumen 38 and into the area distal of the scope body 34 of the endoscope 30. Using the illumination source 40 and the viewing device 42, the physician positions the ligation-cutting tool 200 over the side branch 22 such that the side branch 22 is sitting in the yokes 208 and 210 (see FIG. 11). The physician then manipulates the handle 220 of the ligation-cutting tool 200 to actuate the ligation clip applicator 202. As the prongs 212A and 212B on each of the yokes 208 and 210 move toward each other, the ligation clips 216 are clamped about the side branch 22, thereby stopping blood flow through the side branch 22.

Figure 12:
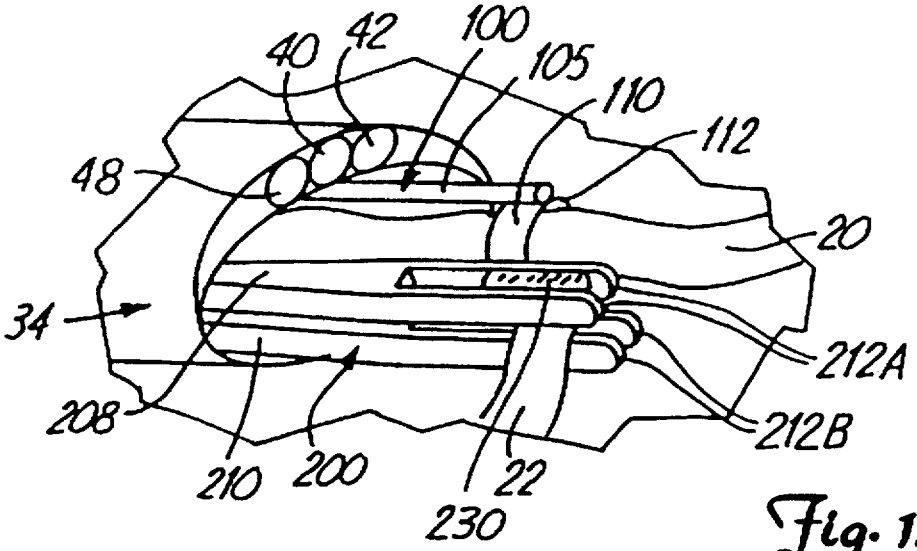

While the side branch 22 is held securely between the yokes 208 and 210 of the ligation clip applicator 202, the physician pushes the plunger 224 to activate the cutting mechanism 204. As shown in FIG. 12, the cutting blade 230 thus moves distally into and through the side branch 22, thereby severing the side branch 22 from the blood vessel 20 between the ligation clips 216. When the plunger 224 is released by the physician, the cutting blade 230 returns to its original retracted position. The handle 220 is then manipulated to separate the prongs 212A and 212B, and the ligation-cutting tool 200 is withdrawn proximally through the lumen 38 of the endoscope 30. The ligation-cutting tool 200 may then be prepared to be used again later in the procedure (i.e., reloaded with additional clips 216), if required.

After the ligation-cutting tool 200 has been removed from the endoscope, the dissecting tool 100 and endoscope 30 are again advanced distally along the blood vessel 20 (as previously described) until another side branch is reached. In this regard, the dissecting ring 110 is large enough to pass over the clipped and severed stumps of any side branches 22 which extend from the blood vessel 20. The ligation-cutting tool 200 is then used as previously described to sever additional side branches from the blood vessel 20. The procedure is repeated until the desired length of blood vessel 20 has been dissected free from the surrounding tissue and side branches. During the dissection procedure, the suction-coagulator tool 300 is used as required to control bleeding, again under the constant vigilance of the physician through the endoscope 30. During the entire procedure, the blood vessel 20 has been held in tension by the physician via the gripping tool 150. In addition, as more and more of the blood vessel 20 becomes dissected, the endoscope 30 is advanced distally into the patient's body and the blood vessel 20 is moved into the lumen 38 of the scope body 34.

When the desired length of blood vessel 20 has been dissected free from the surrounding connective tissue, the dissecting tool 100 is moved proximally away from the distal end of the dissected segment, and the side-biting ligation-cutting tool 250 is inserted into the proximal end of the lumen 38 and advanced distally through the lumen 38 into the area adjacent the distal end of the scope body 34 and the distal end of the dissected blood vessel 20. The side-biting ligation-cutting tool 250 is positioned such that the blood vessel 20 is between the first yoke 258 and the second yoke 260 of the ligation clip applicator 252. When the blood vessel 20 is properly positioned between yokes 258 and 260, the physician manipulates the handle 270 to actuate the ligation clip applicator 252. As the yokes 258 and 260 move toward each other, the yokes 258 and 260 act to pinch the ligation clips 266 over the distal end of the dissected blood vessel 20 (thus stopping blood flow through the blood vessel 20). While the blood vessel 20 is held securely by the ligation clip applicator 252, the physician pushes the plunger 274 to activate the cutting mechanism 254. The cutting blade 280 advances between the ligation clips 266 and through the blood vessel 20 to sever the blood vessel 20 into a freed section 360 having free end 352 (FIG. 10) and a free end 361

Figure 13:
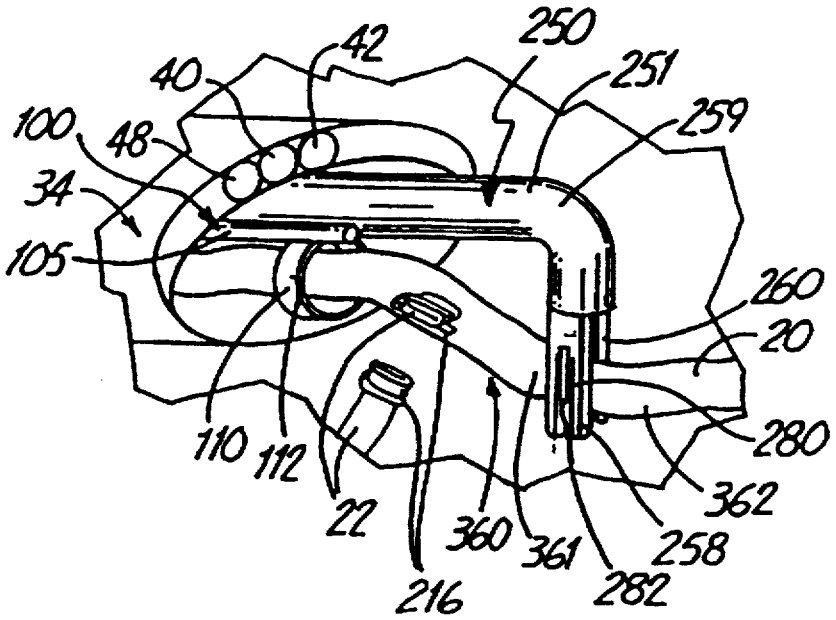

(FIG. 13) and a remaining section 362. When the plunger 274 is released by the physician, the cutting blade 280 returns to its retracted position. The handle 270 is manipulated to separate the prongs 262A and 262B, and the side-biting ligation-cutting tool 250 is withdrawn proximally through the lumen 38 of the endoscope 30. The tool 250 may apply ligation clips on sections 360 and 362, or just one clip on the remaining section 362 of the blood vessel 20.

The freed section 360 of the blood vessel 20 is now free of all connections to the patient's body and is substantially within the lumen 38 of the endoscope 30. While gripping the now dissected blood vessel 20 with the gripping forceps 150, the physician may simultaneously remove the scope body 34 of the endoscope 30 and the enclosed segment of blood vessel 20 from the body of the patient. After the endoscope 30 and freed section 360 of blood vessel 20 are removed from the patient, the physician closes the incision 350 in the patient's body to complete the vessel harvesting procedure. The freed section 360 of the blood vessel 20 may then be removed from the lumen 38 of the endoscope 30 and prepared for its intended end use. The vessel harvesting procedure has been accomplished with only a single small incision, yet the physician can see the entire working portion of the procedure for manipulation of the tools to accomplish dissection, ligation and severing of the freed section 360 of the blood vessel 20. This results in less trauma to the patient than was previously attainable, with a much more precise and efficient procedure, both in terms of affecting the tissue surrounding the dissected vessel, and in terms of the timing and control of the procedure by the physician.

Occasionally, it is desired to remove a continuous length of a blood vessel that is longer than the scope body of the inventive endoscope. In this instance, the physician is unable to advance the endoscope and its related tools far enough from the original small incision into the patient to harvest a segment of the desired length. If no endoscope scope body is long enough to harvest a blood vessel segment of the desired length, the physician may make a second incision in the patient adjacent that point on the blood vessel where the dissection has reached via the use of the endoscope and related tools through the first incision. This is illustrated in FIG. 14.

Figure 14:
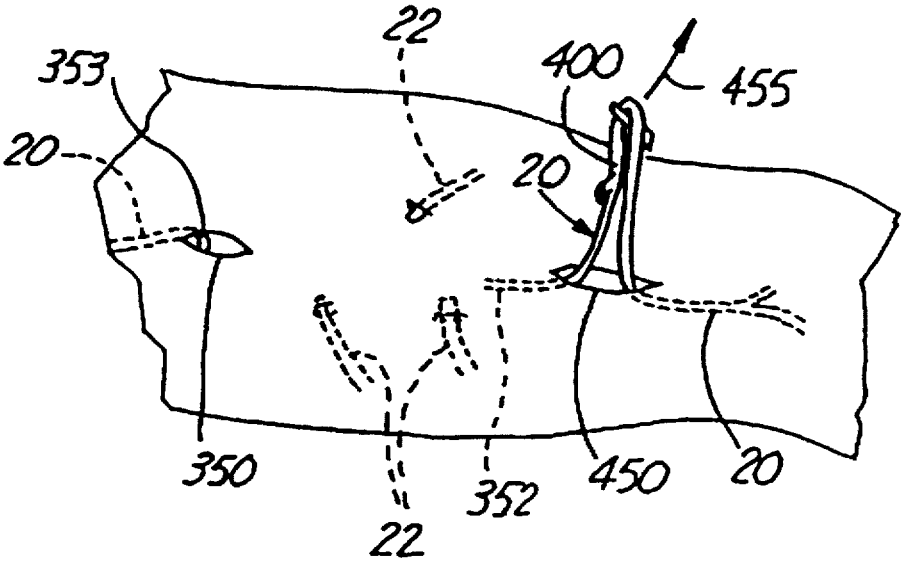
FIG. 14 illustrates the partial removal of a partially dissected blood vessel through a second incision, when a long continuous segment of blood vessel is desired to be dissected from the patient's body.

FIG. 14 illustrates a portion of a patient's leg. A first incision 350 has been made in the patient and the blood vessel 20 severed to create free ends 353 and 352. A portion of the desired segment of the blood vessel (to the left of the incision 350 in FIG. 14) has been dissected, ligated and clipped from the surrounding tissue and side branches 22, using the inventive endoscope and tools in a manner as discussed above. The desired segment of the blood vessel (designated as segment 400 in FIG. 14) is not severed using the side-biting ligation-cutting tool 250 through the scope body 34 of the endoscope 30. Instead, a second incision 450 is made in the patient adjacent that point where the dissection of the blood vessel 20 has reached. This second incision thus exposes that portion of the blood vessel 20 which has been dissected from the surrounding connective tissue of the patient's body (segment 400). The physician releases the free end 352 of the blood vessel 20 (which has been continually held by the gripping forceps 150) and proximally withdraws the endoscope 30 and all of its associated tools which are still in the patient's body. Working through the second incision 450, the physician then grips the exposed portion of the blood vessel 20 and pulls the dissected segment 400 of the blood vessel 20 through the second incision, in direction of arrow 455 as illustrated in FIG. 14.

Once the entire dissected segment 400 has been pulled out of the patient through the second incision 450, further dissection of the remaining portion of the blood vessel 20 within the patient can continue using the inventive tools and method. As previously described, the gripping forceps 150 is inserted through the dissecting ring 110 of the dissecting tool 100 and the assembly of the dissecting tool 100 and the gripping forceps 150 is inserted into the proximal end of the lumen 38 and advanced distally through the lumen 38. The gripping forceps 150 is again used to hold the free end 352 of the segment 400 of the blood vessel 20 during the continued procedure. The endoscope 30 and dissecting tool 100 are distally advanced over the blood vessel 20 and into the patient's body through the second incision 450. The physician then continues to dissect the blood vessel 20 away from the surrounding connective tissue with the dissecting tool 100, ligating and severing side branches 22 as they are encountered using the ligation-cutting tool 150. The suction-coagulator tool 300 is also used as necessary during continued dissection and side branch severing. This process may be repeated until the desired length of blood vessel 20 has been harvested. At this point, the side-biting ligation-cutting tool 250 is employed through the second incision 450 and endoscope 30 to sever the blood vessel 20 from the patient in the desired length. The severed blood vessel is then withdrawn, along with the endoscope 30 and any related tools remaining within the patient, from the patient through the second incision 450. The severed blood vessel is removed from the endoscope and then treated as necessary for further use. The incisions 350 and 450 are then closed up, with minimal trauma to the patient. For instance, a two-step vessel harvesting procedure such as illustrated in FIG. 14 may result in the harvesting of a vessel as long as twelve to fifteen inches, with only two separate 3 cm long incisions made in the patient's skin. The entire procedure, as conducted using the inventive endoscope and its related tools, has been conducted under direct vision or endoscopic vision by the physician and is thus much more effective, efficient and elegant than prior vessel harvesting techniques.

CONCLUSION

The present invention permits a discrete segment of a blood vessel to be harvested with only a small incision in the body of a patient (or more than one small incision if a very long segment is desired). The inventive endoscope and its unique tools eliminate the need for a full length incision along the length of the blood vessel in order to harvest a segment of the blood vessel. Use of the inventive endoscope and tools eliminates the need for a second incision at the distal end of the desired segment of the blood vessel in order to sever the desired segment from the patient's body, and also allows vessel harvesting with a relatively small incision. Proximal incisions heal easier and more readily than distal incisions in most patients, and particularly for those with poor circulation in their extremities. The illumination source and the viewing device of the inventive endoscope allow the physician to directly view the dissection in process, which results in a very precise and controlled dissection of the blood vessel. At the same time, the use of the ligation-cutting tool and the side-biting ligation-cutting tool allows the physician to control bleeding by cutting and sealing off side branches to the blood vessel and the vessel itself in a secure and permanent manner. Nothing is inserted within the blood vessel being harvested during the procedure, so vessel integrity is maintained. Accordingly, undesired trauma to the vessel being harvested and to its surrounding connective tissue is minimized.

Although the present invention has been described with reference to preferred embodiments, workers skilled in the art will recognize that changes may be made in form and detail without departing from the spirit and scope of the invention.

What is claimed:

1. A method of harvesting a section of a vessel from a patient's body as living tissue for use in a different environment of the patient's body comprising:

providing an endoscope of the type having a scope body with a lumen extending longitudinally therethrough, with the lumen having a proximal end and a distal end, and means for viewing an area adjacent the distal end of the lumen, the lumen having a lateral dimension of size sufficient to accommodate the vessel and a tool for use in harvesting the vessel;

exposing a first end of the vessel section to be harvested through an incision in the patient's body;

gripping the first end with a gripping tool that has been inserted through the lumen of the endoscope; and dissecting the vessel away from surrounding connective tissue of the patient's body with a dissecting tool inserted through the lumen of the endoscope, using the viewing means to view the dissection in process;

*cutting the vessel at proximal and distal ends of the vessel section; and*

*removing the vessel section from the patient's body, the steps of exposing, gripping, dissecting, cutting and removing being performed in a manner that minimizes damage to the endothelium of the vessel.*

2. The method of harvesting a vessel according to claim 1, including:

advancing the endoscope and the dissecting tool along the vessel until a side branch of the vessel is encountered.

3. The method of harvesting a vessel according to claim 2, including:

applying a ligation member to the branch and cutting the branch between the vessel and the ligation member with a ligating-cutting tool inserted through the lumen.

4. The method of harvesting a vessel according to claim 3, including:

repeating the advancing and applying steps until the endoscope is fully inserted or a desired length of the vessel is reached.

5. The method of harvesting a vessel according to claim 1, including:

controlling bleeding as necessary with a bleeding control tool inserted through the lumen.

6. The method of harvesting a vessel according to claim 1, including:

ligating and cutting the distal end of the vessel with a transecting tool inserted through the lumen, allowing a segment of the vessel to be removed without making a second incision in the patient's body.

7. The method of harvesting a vessel according to claim 1, including:

making a second incision in the patient's body spaced from the first incision;

exposing that portion of the vessel which has been dissected from surrounding tissue of the patient's body through the second incision in the patient's body;

gripping the exposed portion of the vessel which has been dissected and that has been inserted through the lumen of the endoscope;

advancing the endoscope over the vessel and into the patient's body through the second incision; and continuing to dissect the vessel away from surrounding connective tissue of the patient's body with a dissecting tool inserted through the lumen of the endoscope, using the viewing means to view the continued dissection in process.

8. A method of removing a section of a vessel from a patient's body for use in a different environment comprising:

providing an endoscope of the type having a scope body with a lumen extending longitudinally therethrough, with the lumen having a proximal end and a distal end, and means for viewing an area adjacent to the distal end of the lumen, the lumen having a lateral dimension of size sufficient to accommodate that section of the vessel which is being removed and a tool for use in removing the section of the vessel;

exposing a portion of the section of the vessel to be removed through an incision in the patient's body;

gripping the exposed portion with a gripping tool that has been inserted through the lumen of the endoscope; and dissecting the section of the vessel which is being removed from the patient's body with a dissecting tool also inserted through the lumen of the endoscope, using the viewing means to view the dissection process;

*cutting the vessel at proximal and distal ends of the vessel section; and*

*removing the vessel section from the patient's body, the steps of exposing, gripping, dissecting, cutting and removing being performed in a manner that minimizes damage to the endothelium of the vessel.*

9. The method of removing a section of a vessel according to claim 8, and further including:

removing the section of the vessel through the lumen of the endoscope.

10. The method of removing a section of a vessel according to claim 8, and further including:

advancing the endoscope and the dissecting tool along the vessel until a branch of the vessel is encountered.

11. The method of removing a section of a vessel according to claim 10, and further including:

applying a ligation member to the vessel branch and cutting the branch with a ligating-cutting tool inserted through the lumen.

12. The method of removing a section of a vessel according to claim 11, and further including:

repeating the advancing and applying steps until the endoscope is fully inserted or the desired amount of the vessel is dissected.

13. The method of removing a section of a vessel according to claim 8, and further including:

controlling bleeding as necessary with a bleeding control tool inserted through the lumen.

*14. The method of claim 1 further comprising re-using the vessel section as a fluid conduit in another part of the patient's body.*

*15. The method of claim 8 further comprising re-using the vessel section as a fluid conduit in a human body.*

*16. A method of harvesting a section of a vessel from a patient's body for use in a different environment comprising:*

*making an incision over a first end of the vessel section to be harvested, the length of the incision being sufficient to accommodate at least one tool used in harvesting the vessel section but being substantially smaller than the length of the vessel section;*

*exposing the first end of the vessel section through the incision;*

*dissecting the vessel away from surrounding tissue of the patient's body until a desired length of vessel which exceeds the length of the incision has been dissected free from surrounding tissue;*

*severing the vessel at proximal and distal ends of the vessel section with at least one tool inserted through the incision; and*

*removing the vessel section through the incision, the steps of making an incision, exposing, dissecting, severing, and removing being performed in a manner that minimizes damage to the endothelium of the vessel.*

*17. The method of harvesting a vessel according to claim 16, including:*

*applying a ligation member to the vessel in a position distal to the distal end of the vessel section.*

*18. The method of harvesting a vessel according to claim 16, including;*

*controlling bleeding as necessary.*

*19. The method of harvesting a vessel according to claim 16, including:*

*applying a ligation member to a side branch of the vessel; and*

*severing the side branch of the vessel between the ligation member and the vessel.*

*20. The method of claim 16 further comprising re-using the vessel section as a fluid conduit in a human body.*

*21. The method of claim 16 further comprising re-using the vessel section as a fluid conduit in another part of the patient's body.*

*22. A method of harvesting a section of a vessel from a patient's body for use in a different environment comprising:*

*making an incision in the patient's body over a first end of the vessel section to be harvested, the length of the incision being sufficient to accommodate at least one tool used in harvesting the vessel section but being substantially smaller than the length of the vessel section;*

*exposing the first end of the vessel section to be harvested through the incision in the patient's body;*

*dissecting the vessel away from surrounding tissue of the patient's body; and*

*viewing the dissection of the vessel with a viewing device inserted through the incision;*

*severing the vessel at proximal and distal ends of the vessel section; and*

*removing the vessel section from the patient's body, the steps of making an incision, exposing, dissecting, viewing, severing and removing being performed in a manner that minimizes damage to the endothelium of the vessel.*

*23. The method of harvesting a vessel according to claim 22, including:*

*applying a ligation member to a side branch of the vessel; and*

*severing the side branch between the vessel and the ligation member.*

*24. The method of harvesting a vessel according to claim 23, including;*

*repeating the dissecting step until a desired length of the vessel section has been dissected.*

*25. The method of harvesting a vessel according to claim 24, including:*

*severing the distal end of the vessel section; and*

*removing the vessel section through the incision.*

*26. The method of harvesting a vessel according to claim 22, including;*

*repeating the dissecting step until a desired length of the vessel section has been dissected.*

*27. The method of harvesting a vessel according to claim 26, including:*

*severing the distal end of the vessel section; and*

*removing the vessel section through the incision.*

*28. The method of harvesting a vessel according to claim 22, including:*

*controlling bleeding as necessary.*

*29. The method of claim 20 further comprising re-using the vessel section as a fluid conduit in a human body.*

*30. The method of claim 22 further comprising re-using the vessel section as a fluid conduit in another part of the patient's body.*

*31. A method of harvesting a section of a vessel from a patient's body for use in a different environment comprising:*

*providing a device having an elongated body, the body having a lumen extending longitudinally therethrough, the lumen having a proximal end and a distal end and having a lateral dimension of size sufficient to accommodate the vessel and a tool for use in harvesting the vessel;*

*exposing a first end of the vessel section to be harvested through an incision in the patient's body;*

*gripping the first end with a gripping tool that has been inserted through the lumen of the elongated body;*

*dissecting the vessel away from surrounding tissue of the patient's body with a dissecting tool inserted through the incision; and*

*viewing the dissection of the vessel from an area adjacent the distal end of the lumen of the elongated body;*

*severing the vessel at proximal and distal ends of the vessel section; and*

*removing the vessel section from the patient's body, the steps of exposing, gripping, dissecting, viewing, severing and removing being performed in a manner that minimizes damage to the endothelium of the vessel.*

*32. The method of harvesting a vessel according to claim 31, including:*

*advancing the elongated body and the dissecting tool along the vessel until a side branch of the vessel is encountered.*

*33. The method of harvesting a vessel according to claim 32, including:*

*applying a ligation member to the branch and cutting the branch between the vessel and the ligation member with a ligating-cutting tool inserted through the lumen.*

*34. The method of harvesting a vessel according to claim 33, including:*

*repeating the advancing and applying steps until the elongated body is fully inserted or a desired length of the vessel is reached.*

*35. The method of harvesting a vessel according to claim 31, including:*

*controlling bleeding as necessary with a bleeding control tube inserted through the lumen.*

*36. The method of harvesting a vessel according to claim 31, including:*

*ligating and cutting the distal end of the vessel with a transecting tool inserted through the lumen, allowing the vessel section to be removed without making a second incision in the patient's body.*

*37. The method of harvesting a vessel according to claim 31, including:*

*making a second incision in the patient's body spaced from the first incision;*

*exposing that portion of the vessel which has been dissected from surrounding tissue of the patient's body through the second incision in the patient's body;*

*gripping the exposed portion of the vessel which has been dissected with a gripping tool that has been inserted through the lumen of the elongated body;*

*advancing the elongated body over the vessel and into the patient's body through the second incision; and*

*continuing to dissect the vessel away from surrounding tissue of the patient's body with a dissecting tool inserted through the second incision.*

*38. The method of claim 31 further comprising re-using the vessel section as a fluid conduit in a human body.*

*39. The method of claim 3 further comprising re-using the vessel section as a fluid conduit in another part of the patient's body.*

*40. A method of harvesting a section of a vessel from a patient's body for use in a different environment comprising:*

*making an incision over a first end of the vessel section to be harvested, the length of the incision being sufficient to accommodate at least one tool used in harvesting the vessel section but being substantially smaller than the length of the vessel section;*

*exposing the first end of the vessel section through the incision;*

*dissecting the vessel away from surrounding tissue of the patient's body with a dissecting tool inserted through the incision until a desired length of vessel which exceeds the length of the incision has been dissected free from surrounding tissue;*

*viewing the dissection of the vessel with a viewing device inserted through the incision;*

*severing the vessel at proximal and distal ends of the vessel; and*

*removing the vessel section from the patient's body, the steps of making an incision, exposing, dissecting, viewing, severing, and removing being performed in a manner that minimizes damage to the endothelium of the vessel.*

*41. The method of claim 40 further comprising re-using the vessel section as a fluid conduit in a human body.*

*42. The method of claim 40 further comprising re-using the vessel section as a fluid conduit in another part of the patient's body.*

*43. The method of harvesting a vessel according to claim 40, including:*

*applying a ligation member to the vessel in a position distal to the distal end of the vessel section.*

*44. The method of harvesting a vessel according to claim 40, including;*

*controlling bleeding as necessary.*

*45. The method of harvesting a vessel according to claim 40, including:*

*litigating a branch of the vessel; and*

*severing the branch of the vessel between the ligation and the vessel.*

*46. The method of harvesting a vessel according to claim 40 including maintaining the lumen of the vessel clear of any tools and other objects used in the harvesting procedure.*

*47. The method of harvesting a vessel according to claim 40 including making a second incision in the patient's body spaced from the first incision, the second incision being substantially smaller than the length of the vessel section, and wherein the vessel section is removed through the second incision.*

*48. A method of harvesting a section of a vessel from a patient's body for use in a different environment comprising:*

*making an incision over a first end of the vessel section to be harvested, the length of the incision being sufficient to accommodate at least one tool used in harvesting the vessel section but being substantially smaller than the length of the vessel section;*

*exposing the first end of the vessel section through the incision;*

*dissecting the vessel away from surrounding tissue of the patient's body until a desired length of vessel which exceeds the length of the incision has been dissected free from surrounding tissue;*

*severing the vessel at proximal and distal ends of the vessel section with at least one tool inserted through the incision;*

*removing the vessel section through the incision; and*

*re-using the vessel section as a fluid conduit in a human body.*

*49. A method of harvesting a section of a vessel from a patient's body for use in a different environment comprising:*

*making an incision in the patient's body over a first end of the vessel section to be harvested, the length of the incision being sufficient to accommodate at least one tool used in harvesting the vessel section but being substantially smaller than the length of the vessel section;*

*exposing the first end of the vessel section to be harvested through the incision in the patient's body;*

*dissecting the vessel away from surrounding tissue of the patient's body; and*

*viewing the dissection of the vessel with a viewing device inserted through the incision;*

*severing the vessel at proximal and distal ends of the vessel section;*

*removing the vessel section from the patient's body; and*

*re-using the vessel section as a fluid conduit in a human body.*

*50. A method of harvesting a section of a vessel from a patient's body for use in a different environment comprising:*

*providing a device having an elongated body, the body having a lumen extending longitudinally therethrough, the lumen having a proximal end and a distal end and having a lateral dimension of size sufficient to accommodate the vessel and a tool for use in harvesting the vessel;*

*exposing a first end of the vessel section to be harvested through an incision in the patient's body;*

*gripping the first end with a gripping tool that has been inserted through the lumen of the elongated body;*

*dissecting the vessel away from surrounding tissue of the patient's body with a dissecting tool inserted through the incision; and*

*viewing the dissection of the vessel from an area adjacent the distal end of the lumen of the elongated body;*

*severing the vessel at proximal and distal ends of the vessel section;*

*removing the vessel section from the patient's body; and*

*re-using the vessel section as a fluid conduit in a human body.*

*51. A method of harvesting a section of a vessel from a patient's body for use in a different environment comprising:*

*making an incision over a first end of the vessel section to be harvested, the length of the incision being sufficient to accommodate at least one tool used in harvesting the vessel section but being substantially smaller than the length of the vessel section;*

*exposing the first end of the vessel section through the incision;*

*dissecting the vessel away from surrounding tissue of the patient's body with a dissecting tool inserted through the incision until a desired length of vessel which exceeds the length of the incision has been dissected free from surrounding tissue;*

*viewing the dissection of the vessel with a viewing device inserted through the incision;*

*severing the vessel at proximal and distal ends of the vessel;*

*removing the vessel section from the patient's body; and*

*re-using the vessel section as a fluid conduit in a human body.*

*52. A method of re-using a section of a vessel from a patient's body in the patient's body comprising:*

*making an incision over a first end of the vessel section, the length of the incision being sufficient to accommodate at least one tool used in the method but being substantially smaller than the length of the vessel section;*

*exposing the first end of the vessel section through the incision;*

*dissecting the vessel away from surrounding tissue of the patient's body with a tool inserted through the incision until a desired length of vessel which exceeds the length of the incision has been dissected free from surrounding tissue;*

*severing the first end of the vessel section with a tool inserted through the incision; and*

*re-using the vessel section as a fluid conduit in the patient's body.*

* * * * *